United States Patent
Huang et al.

(10) Patent No.: US 7,425,202 B2
(45) Date of Patent: Sep. 16, 2008

(54) NON-SEEDING BIOPSY DEVICE AND METHOD

(75) Inventors: Alexander Huang, Menlo Park, CA (US); Henry Lao, Sunnyvale, CA (US); David Needleman, Sausalito, CA (US)

(73) Assignee: Percutaneous Systems, Inc., Mountain View, CA (US)

( * ) Notice: Subject to any disclaimer, the term of this patent is extended or adjusted under 35 U.S.C. 154(b) by 7 days.

(21) Appl. No.: 10/794,317

(22) Filed: Mar. 5, 2004

(65) Prior Publication Data

US 2005/0197595 A1    Sep. 8, 2005

(51) Int. Cl.
*A61B 10/00* (2006.01)
(52) U.S. Cl. ............................ 600/564; 600/567
(58) Field of Classification Search ......... 600/562–568, 600/121, 123, 124; 604/95.01
See application file for complete search history.

(56) References Cited

U.S. PATENT DOCUMENTS

| | | | | |
|---|---|---|---|---|
| 724,913 | A | * | 4/1903 | Montgomery ............... 604/278 |
| 3,168,092 | A | | 2/1965 | Silverman |
| 3,421,509 | A | | 1/1969 | Fiore |
| 3,589,356 | A | | 6/1971 | Silverman |
| 3,719,190 | A | * | 3/1973 | Avery ......................... 607/122 |
| 4,043,345 | A | | 8/1977 | Kramann et al. |
| 4,262,677 | A | | 4/1981 | Bader |
| 4,657,020 | A | * | 4/1987 | Lifton ......................... 606/106 |
| 4,741,326 | A | * | 5/1988 | Sidall et al. ................. 600/123 |
| 4,772,260 | A | * | 9/1988 | Heyden ....................... 604/45 |
| 4,958,625 | A | | 9/1990 | Bates et al. |
| 5,037,379 | A | | 8/1991 | Clayman et al. |
| 5,090,419 | A | | 2/1992 | Palestrant |
| 5,190,561 | A | * | 3/1993 | Graber ........................ 606/127 |
| 5,368,045 | A | | 11/1994 | Clement et al. |
| 5,431,676 | A | | 7/1995 | Dubrul et al. |
| 5,454,790 | A | | 10/1995 | Dubrul |
| 5,531,717 | A | | 7/1996 | Roberto et al. |
| 5,676,688 | A | | 10/1997 | Jaker et al. |
| 5,711,841 | A | | 1/1998 | Jaker |
| 5,792,114 | A | | 8/1998 | Fiore |

(Continued)

FOREIGN PATENT DOCUMENTS

DE    10031661 A1    1/2002

(Continued)

OTHER PUBLICATIONS

Woitzik et al., "Polyethylene sheath device to reduce tumor cell seeding along the needle tract in percutaneous biopsy," (2003) *Surg. Endosc.* 17:311-314.

*Primary Examiner*—Max Hindenburg
*Assistant Examiner*—Jonathan M Foreman
(74) *Attorney, Agent, or Firm*—Townsend and Townsend and Crew, LLP (57) ABSTRACT

Tissue biopsy is performed through a central passage of a cannula covered with a protective sleeve. The protective sleeve is attached at one end to a location at or near a distal end of the cannula. After the biopsy procedure is completed, the cannula is withdrawn so that its exterior slides through the sleeve. In this way, the trailing edge of the sleeve is invaginated within the proximal portions of the itself to envelop the sleeve exterior and reduce the risk of inadvertent tumor cell seeding.

9 Claims, 5 Drawing Sheets

U.S. PATENT DOCUMENTS

| | | |
|---|---|---|
| 5,814,058 A | 9/1998 | Carlson et al. |
| 5,836,913 A | 11/1998 | Orth et al. |
| 5,897,535 A | 4/1999 | Feliziani et al. |
| 6,007,488 A | 12/1999 | Jaker et al. |
| 6,007,521 A | 12/1999 | Bidwell et al. |
| 6,022,362 A | 2/2000 | Lee et al. |
| 6,080,174 A | 6/2000 | Dubrul et al. |
| 6,217,569 B1 | 4/2001 | Fiore |
| 6,240,968 B1 | 6/2001 | Bigonzi-Jaker et al. |
| 6,325,812 B1 | 12/2001 | Dubrul et al. |
| 6,344,026 B1 | 2/2002 | Burbank et al. |
| 6,485,409 B1 | 11/2002 | Voloshin et al. |
| 6,494,893 B2 | 12/2002 | Dubrul et al. |
| 6,506,179 B1 * | 1/2003 | Tiefenthal et al. ...... 604/103.06 |
| 6,585,721 B2 | 7/2003 | Fiore |
| 6,908,428 B2 | 6/2005 | Aizenfeld et al. |
| 6,988,988 B2 | 1/2006 | Voloshin et al. |
| 2001/0044595 A1 * | 11/2001 | Reydel et al. ............ 604/98.02 |
| 2002/0095100 A1 * | 7/2002 | Lee et al. .................... 600/564 |

FOREIGN PATENT DOCUMENTS

| | | |
|---|---|---|
| EP | 605427 B1 | 12/1992 |

* cited by examiner

NON-SEEDING BIOPSY DEVICE AND METHOD

BACKGROUND OF THE INVENTION

1. Field of the Invention

The present invention relates generally to medical apparatus and methods. More particularly, the present invention relates to a method and system for accessing a biopsy site in solid tissue while protecting the access tract from seeding with tumor cells.

Percutaneous or "needle" biopsy of suspected malignancies is now in common use. Typically, an access sheath, such as a needle or cannula, is introduced through solid tissue to provide access to a target site in the tissue. A biopsy needle, biopsy gun, or similar device is then introduced through the needle or cannula to obtain a small tissue sample. The biopsy device is withdrawn through the needle or cannula, and the needle or cannula then withdrawn through the tissue tract to complete the procedure. The needle or cannula may also be incorporated as an integral portion of the biopsy device.

While quite useful and generally successful, such "needle biopsy" procedures raise concern over possible "seeding" of tumor cells along the tissue tract by the needle or cannula as it is withdrawn. Seeding refers to the unintentional transport of cells from the biopsy site into the tissue tract. Such seeding can inadvertently spread the tumor beyond its original location, making treatment of the tumor more difficult.

The use of a separate needle or cannula is advantageous since it allows multiple biopsy samples to be taken from the same location without the need to form a separate puncture for each sample. Integral systems where the needle or cannula is part of the biopsy device require separate punctures to be formed, but it can be manufactured with smaller diameters than biopsy systems including separate access sheaths and biopsy components. Biopsy systems including separate access sheaths are further advantageous in that the access sheath isolates the tissue tract from the biopsy-capturing component of the system. The relatively large size of the access sheath, however, can itself dislodge tumor cells and potentially seed the tissue tract when the access sheath is removed.

In order to minimize the risk of tumor cell seeding in biopsy tissue tracts, placement of a sheath over the biopsy instrument has been proposed by Woitzik and Krauss, *Surgical Endoscopy* (2003) 17:311-314. A polyethylene sheath is positioned so that it covers the exterior and interior of an access cannula, i.e., by folding the sheath over the leading (distal) end of the cannula. The cannula is introduced to a target site using a stylet in a generally conventional manner. After taking a sample through the lumen of the cannula with a separate biopsy instrument, the biopsy instrument is removed, and the inside of the sleeve (i.e. that portion which passes through the lumen of the cannula) is pulled back through the cannula lumen to remove the cannula. In this way, the sheath on the exterior of the cannula is inverted or invaginated into the lumen of the cannula as the sheath is withdrawn. Any tumor cells which might adhere to the exterior of the cannula after the biopsy has been completed will be drawn into the lumen of the cannula, thus reducing the risk of tumor cell seeding.

While the cannula and method of Woitzik and Krauss will theoretically limit the risk of tumor cell seeding of tissue tracts, the particular approach suffers from certain disadvantages. The sheath which is present in the lumen of the cannula can be damaged by passage of the stylet and/or the biopsy instrument through the cannula. Should the sheath be damaged, it is possible that the sheath will break as it is being pulled, thus preventing complete invagination of the sheath as the cannula is withdrawn. Moreover, folding of the sheath over the distal end of the cannula requires that the cannula tip be blunt. Such a blunt tip prevents designs having sharpened or other self-introducing designs. Additionally, in order for the exposed sheath portion of Woitzik and Krauss to be isolated within the device, the cannula sheath cannot be allowed to simultaneously move proximally in the tissue tract. Such simultaneous movement would allow exposed sheath portions to contact and potentially seed the tissue tract in a manner analogous to unsheathed access cannula. For that reason, the Woitzik and Krauss cannula must be pushed forwardly (i.e., in a direction into the body) while being pulled out of the body by the inverting sheath. Thus, the apparatus must be pushed and pulled at the same time, which is not always an easy step to perform. Moreover, the forward pressure of the cannula exerts significant friction against the sheath as it is everted. This is both difficult and significantly increases the risk of tearing the sheath as the cannula is being withdrawn.

For these reasons, it would be desirable to provide additional and improved tissue biopsy systems which reduce the risk of tumor cell seeding of percutaneous tissue access tracts. It would be further desirable to provide systems and methods employing access cannulas where the cannula is covered with a protective sleeve which is not located within a lumen of the cannula and which does not need to be folded over a leading or distal tip of the cannula. It would further be desirable to provide cannulas having protective sleeves where withdrawal of the cannula removes the sleeve in a manner which reduces the risk of tumor cell seeding and which pulls only the trailing edge of the sleeve as the cannula is withdrawn. At least some of these objectives will be met by the inventions described hereinbelow.

2. Description of the Background Art

The use of sleeves for protecting biopsy needles and cannulas is described in U.S. Pat. Nos. 4,262,677; 5,037,379; DE 10031661A1; and Woitzik and Krauss (2003) Surg. Endosc. 17:311-314. Biopsy needles are described in U.S. Pat. Nos. 4,958,625; 5,090,419; and 5,368,045. Other biopsy devices having collection bags are described in U.S. Pat. Nos. 6,344,026 and 6,022,362. The use of an everting sleeve composed of thin, tensilized polytetrafluoroethylene for introducing catheters to body lumens is described in U.S. Pat. Nos. 5,531,717; 5,676,688; 5,711,841; 5,897,535; 6,007,488; 6,240,968; and EP605427B1. The use of braided and other radially expanding sleeves for introducing sheaths, surgical tools, and other articles is described in U.S. Pat. Nos. 5,431,676; 5,454,790; 5,814,058; 5,836,913; 6,080,174; 6,325,812; and 6,494,893. A biopsy device with a removable sheath is commercially available from Boston Scientific, under the tradename "ASAP Detachable Biopsy System."

BRIEF SUMMARY OF THE INVENTION

The present invention provides improved methods and systems for performing percutaneous tissue biopsy with reduced risk of tumor cell seeding. The method and system are useful for biopsy of virtually any solid tissue site where conventional needle biopsies may be performed, including breast biopsy, liver biopsy, renal biopsy, and the like.

The systems of the present invention comprise at least a cannula and a protective sleeve positionable over the exterior of the cannula. The systems may optionally include a stylet or other component for facilitating percutaneous introduction of the cannula, a biopsy instrument, instructions for use, packaging, etc. In use the protective sleeve will be located over at least a distal length of the cannula but will usually not be positioned within any portion of the inner lumen of the cannula. In particular, a distal end of the protective sleeve will usually be fixed at or near a distal end or tip of the cannula so that the sleeve will extend proximally to cover some or all of the exterior portions of the cannula proximal to the attachment point. The length of the protective sleeve will preferably be sufficient to cover all proximal portions of the catheter which will potentially contact solid tissue as the distal tip of the cannula is advanced to the target site in solid tissue.

The protective sleeve may be deployed over the outside of the cannula prior to introducing the catheter through tissue, for example being deployed over the cannula at the time of manufacture or by the physician immediately prior to use. More commonly, however, the protective sleeve will be provided in a furled configuration, where the sleeve is unfurled as the cannula is advanced through tissue, i.e. the cannula will pull on the sleeve and "tow" the sleeve into the tissue as the cannula is advanced. Typically, the furled sleeves will be contained in a separate canister or container, with an exemplary "egg" structure being shown in the drawings hereinafter. Providing the protective sleeve in a furled configuration is advantageous because it facilitates handling of the sleeve and minimizes contact of the sleeve with external body structures, thus limiting the risk of contaminating the sleeve before it is introduced to the tissue tract. Separating the sleeve from the cannula as the cannula is introduced also facilitates handling of the cannula since those portions not introduced into tissue will be directly manipulable, i.e., not encased in a slippery, loose-fitting sleeve.

The sleeve may be composed of a variety of materials, including polytetrafluoroethylene (PTFE), perfluoroalkoxy (PFA), high-density polyethylene (HDPE), low-density polyethylene (LDPE), cellulose, and the like. Preferably, the sleeve material will be generally lubricious so that it may pass through tissue with a relatively low friction. In preferred embodiments, however, the protective sleeve will have an interior surface which contacts the exterior of the cannula where at least a portion of the interior surface of the sleeve is treated to have a lower sliding friction than the sliding friction between the outer sleeve surface and the tissue. This difference in sliding frictions is advantageous because it reduces the chance that withdrawal of the cannula will inadvertently pull proximal portions of the sleeve outwardly through the tissue (as may occur with the Woitzik and Krauss sleeve described above). It will be appreciated that only the trailing edge of the sleeve should be pulled by the cannula so that the sleeve is invaginated into its own lumen, thus capturing and removing any tumor cells which might be present on the exterior of the sleeve. Any unintended adherence between the exterior of the cannula and the interior of the protective sleeves could interfere with such intended withdrawal. Optionally, the interior of the sleeve and/or exterior of the cannula could be treated with lubricated materials to reduce sliding friction. Suitable lubricating materials include silicones, such as (MDX).

Friction between the outer sleeve surface and tissue relative to that between the inner sleeve surface and cannula may be adjusted by texturing the various sliding surfaces. For example, by providing a smooth outer sleeve surface, friction with the tissue tract as the cannula is introduced will be reduced. In contrast, if both the inner sleeve surface and the outer cannula surface are smooth, the sleeve and cannula will tend to adhere. Thus, to increase the friction between the tissue and outer sleeve surface and reduce the friction between the outer cannula surface and the inner sleeve surface (which is the most desirable condition), it will generally be desirable to either texture the inner diameter of the protective sleeve or texture the outer diameter of the cannula (but not both). If both sides of the sleeve were textured, friction between the sleeve and the cannula would be increased (which is not desirable).

In some instances, it might be also be desirable to introduce "directional variation" in the friction presented by the sleeve. For example, it would be useful to modify an outer surface of the sleeve so that it experiences low friction as it penetrates tissue but presents higher friction if it is withdrawn from tissue. Such frictional characteristics would facilitate tissue penetration as well as helping immobilize the sleeve as the cannula is withdrawn. Such directional variation can be achieved, for example, by texturing the outer surface of the protective sleeve in a fish-scale or angled barb pattern to allow penetration of the sleeve and inhibit withdrawal of the sleeve through tissue. The texture on the outer surface of the sleeve will increase sliding friction in one direction compared to the other direction.

The protective sleeves will typically be formed from a polymer, with preferred polymers being listed above. The polymers will be extruded or otherwise formed as a tube with a wall thickness in the range from about 0.01 mm to 0.05 mm, preferably being in the range from 0.015 mm to 0.025 mm. The polymer or other sleeve material should, of course, be impermeable to cell passage so that any tumor cells trapped within the sleeve will not inadvertently escape through the sleeve wall.

Specific methods according to the present invention for obtaining a sample from solid tissue comprise accessing a site in the solid tissue with a cannula covered by a protective sleeve. A sample is obtained through a central passage of the cannula (which is preferably not covered by any portion of the sleeve). After the local sampling is completed, the cannula is withdrawn. A distal region of the cannula is fixedly attached to a distal portion of a sleeve, so that the distal portion of the protective sleeve is pulled by the attached end of the cannula to inwardly evert or fold within itself as the cannula is withdrawn. In certain preferred embodiments, a sliding friction between the sleeve and the cannula is less than the sliding friction between the sleeve and the tissue, so that axial sliding of the sleeve in tissue is inhibited. Typically, accessing the site comprises advancing the cannula with a stylet positioned in the central passage. The stylet has a tip which is sharpened or otherwise modified to promote tissue penetration and extends distally beyond the distal end of the cannula. Alternatively, the distal end of the cannula may be sharpened or otherwise modified to enhance tissue penetration so that the cannula becomes "self-penetrating".

The sample may be obtained by any manner which may be performed through the central passage of the cannula. Typically, a biopsy needle, biopsy gun, or other conventional biopsy instrument is passed through the cannula and used to obtain the tissue sample. In some instances, the stylet itself may be used to capture the sample, i.e. using a recess formed on the stylet. Optionally, multiple samples from the same location may be obtained by reinserting the same or a different biopsy device through the cannula while the cannula remains substantially immobile.

Methods according to the present invention for obtaining a sample from solid tissue may also comprise accessing a site in the solid tissue with a cannula covered with a protective sleeve and obtaining the sample through a central passage of the cannula. The cannula is withdrawn through the protective sleeve, where sliding friction between the sleeve and the cannula is less than a sliding friction between the sleeve and the tissue, so that axial sliding of the sleeve in the tissue is inhibited. Other preferred aspects of this second method are generally as described above in connection with the first exemplary method of the present invention.

Systems according to the present invention comprise a cannula having a proximal end, a distal end, and a central passage therethrough. A protective sleeve having a proximal end and a distal end is disposable over an exterior of the cannula, where the distal end is attachable to a location near the distal end of the cannula. The system may further comprise a stylet removably receivable in the central passage of the cannula. Alternatively, the distal end or tip of the cannula may be sharpened or otherwise modified to permit self-penetration through tissue.

Other preferred aspects of the systems of the present invention have been described above.

DETAILED DESCRIPTION OF THE INVENTION

Figure 1:
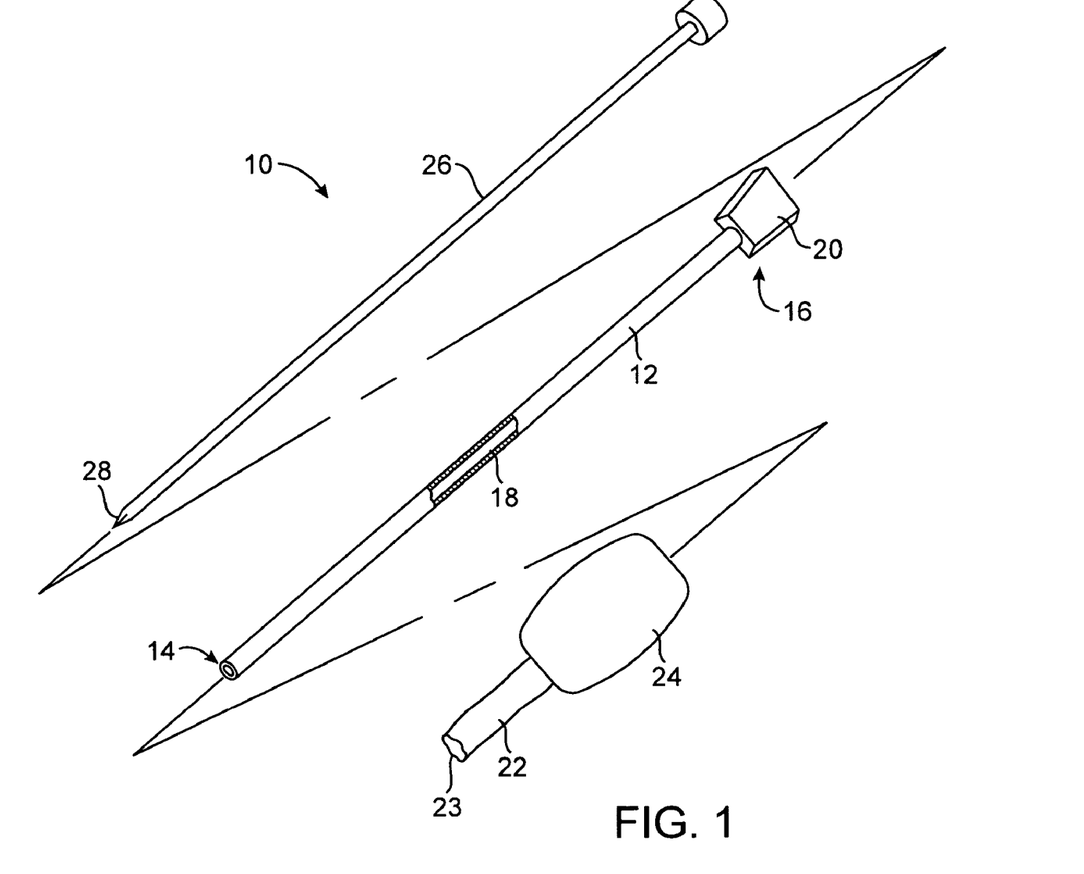
FIG. 1 illustrates an exemplary system for obtaining samples from solid tissue constructed in accordance with the principles of the present invention.

An exemplary system 10 constructed in accordance with the principles of the present invention includes a cannula 12 having a distal end 14, a proximal end 16, a central passage 18 therethrough, and a hub 20 at the proximal end. This will be described in more detail below. The lumen 18 permits introduction of a separate tissue biopsy instrument (not shown) for obtaining a tissue sample when the cannula is positioned adjacent a target site within solid tissue. Usually, a separate stylet 26 (described below) will also be provided to facilitate introduction of the cannula into tissue.

Figure 3A:
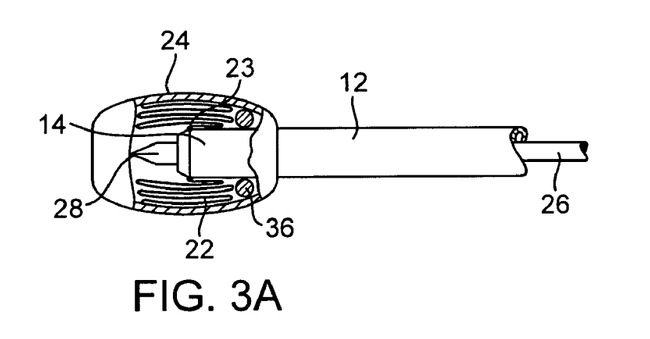
FIGS. 3A and 3B illustrate the construction and use of a furled protective sleeve in the system of FIG. 1.

The system 10 further comprises a protective sleeve 22 which is preferably stowed within a canister 24 or other protective enclosure. The protective sleeve 22 is preferably furled, as best shown in FIG. 3A, and a leading edge 23 of the sleeve is attachable at or near the distal end 14 of the cannula 12. Usually, the leading edge 23 will be attached at or near the distal end of the cannula 12 at the time of manufacture of the system. Alternatively, the leading edge 23 could be modified so that the distal end 14 of cannula 12 engages and captures the leading edge as the cannula is advanced through the canister 24 (although this embodiment is not illustrated).

Figure 2A:
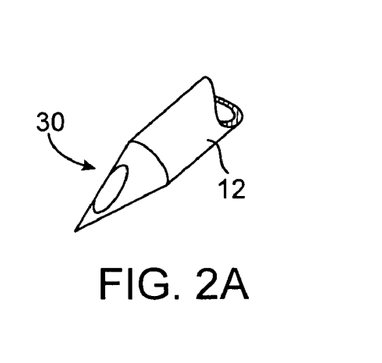
FIGS. 2A and 2B illustrate alternative constructions of the distal end of the cannula of the system of FIG. 1.
Figure 2B:
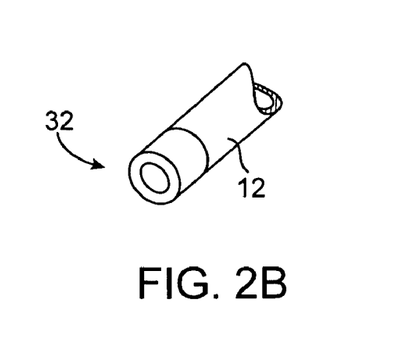
Figure 3B:
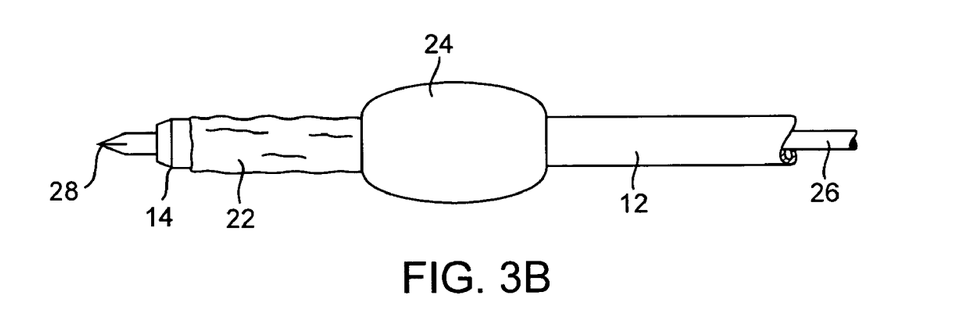

The system 10 will usually include a component or system modification which permits introduction of the cannula 12 through the solid tissue to the desired tissue site. Usually, the system will include a stylet 26 which is removably received within the lumen 18 of the cannula 12 so that a sharpened tip 28 of the stylet projects distally from the distal end 14, as best shown in FIG. 3B. Alternatively, the distal end of the cannula 12 may be modified to have a sharpened tip 30, as shown in FIG. 2A, an electrosurgical tip 32, as shown in FIG. 2B, or in other ways which permit self-penetration of the cannula through solid tissue.

Referring again to FIGS. 3A and 3B, the cannula 12 will pass through an O-ring 36 or other structure intended to increase friction as the cannula is advanced through the canister 24 to deploy the protective sleeve 22. Such increased friction enhances the ability of the surgeon to "tactilely" manipulate the cannula 12 as it is being advanced. Without the increase in friction provided by the O-ring, or other equivalent structure, the cannula would be much harder to manually control, increasing the likelihood that the cannula 12 and protective sleeve 22 would be inadvertently withdrawn from the tissue tract as it is being created. Such inadvertent advancement and retraction would increase the likelihood of tumor cell seeding, contrary to the intention of the present invention. The canister 24 may also be used to help position or record the depth of penetration of the cannula as it is introduced beneath a tissue surface. For example, the canister 24 may be positioned above the tissue surface by a measured distance (optionally including a scale or measured positioning mechanism) to provide a marker, reading, indicia, or other indication of the depth of the distal end of the cannula beneath the tissue surface.

Figure 4:
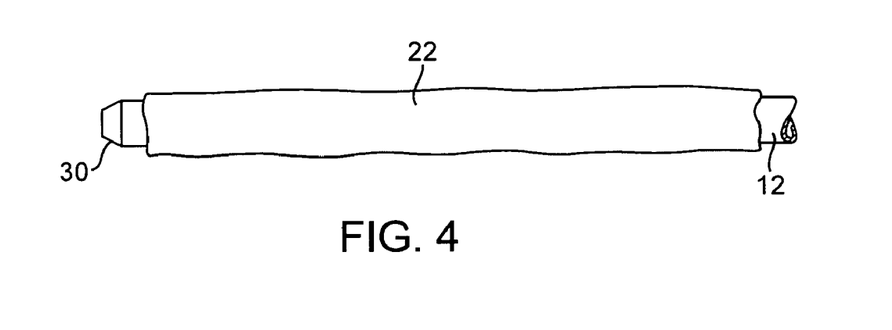
FIG. 4 illustrates an alternative protective sleeve configuration where the sleeve is pre-deployed over the cannula.

While the use of a canister 24 or other enclosure for holding a furled protective sleeve is generally preferred, it is also possible to pre-deploy the protective sleeve 22 over the cannula 12, as shown in FIG. 4. Such pre-deployed protective sleeves may be placed over the cannula at the time of manufacture, may be placed over the cannula immediately prior to use by the user, or may be even deployed from a canister 24 prior to use so that the sleeve is fully deployed prior to introduction to the cannula into tissue. If the sleeve is to be pre-deployed, the pre-deployment will usually be accomplished at the time the system is manufactured, and the system will be shipped with the sleeve 22 over the cannula (without a canister), typically in a sterile package.

Referring now to FIGS. 5A through 5F, use of the system 10 for obtaining a tissue sample from a target site TS in solid tissue T will be described. Initially, the protective sleeve canister 24 is located over a surface of the tissue T which is aligned with the target site TS in a pre-determined manner. Usually, the location of the target site will have been previously determined by fluoroscopic, ultrasonic, MRI, CT, or other conventional imaging techniques.

Figure 5A:
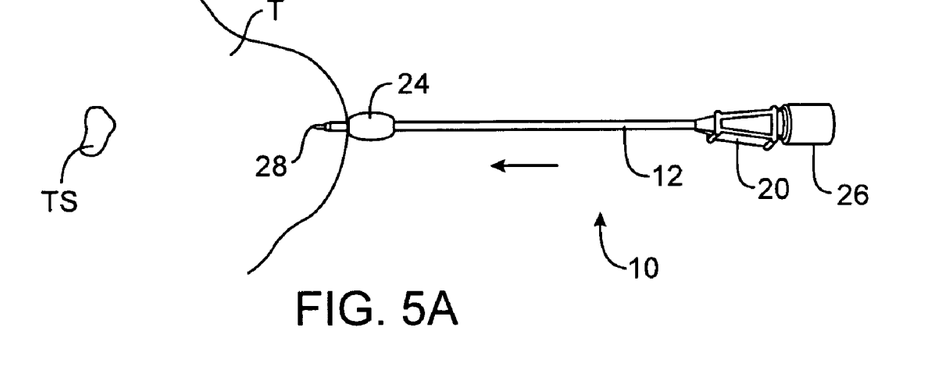
FIGS. 5A through 5F illustrate use of the system of FIG. 1 for obtaining a biopsy sample from a target site in solid tissue.
Figure 5B:
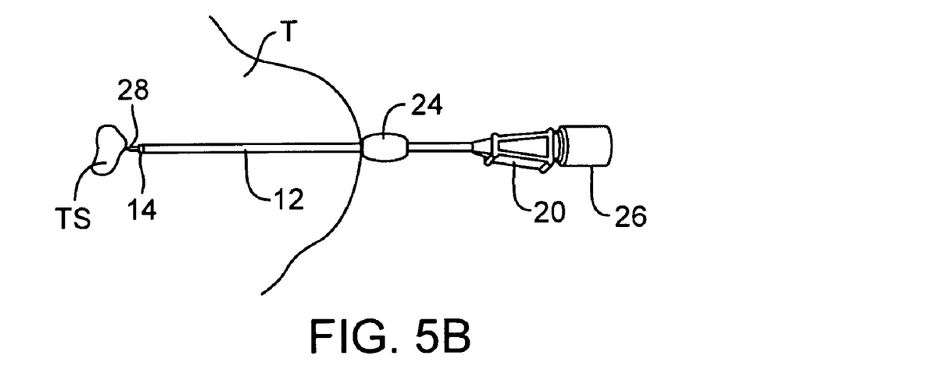
Figure 5C:
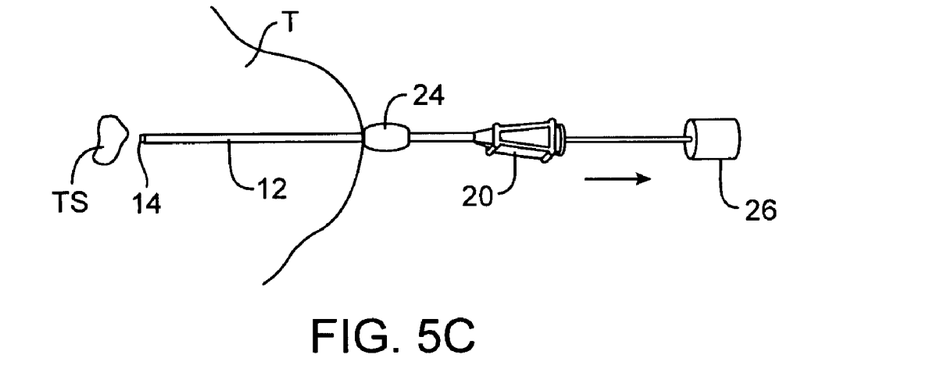

After positioning the canister 24, the cannula 12 is advanced in the direction of the arrow in FIG. 5A so that the sharpened tip 28 of the stylet 26 permits advancement of the cannula through tissue. (A cannula having a self-penetration tip would be advanced similarly.) The cannula 12 is advanced until the distal end 14 reaches a position adjacent to the target site TS, as shown in FIG. 5B. The stylet is then withdrawn in the direction of the arrow shown in FIG. 5C, leaving the cannula 12 in place with a vacant passage 18 to provide access for a biopsy tool 50 (FIG. 5D) to reach the target site TS.

Figure 5D:
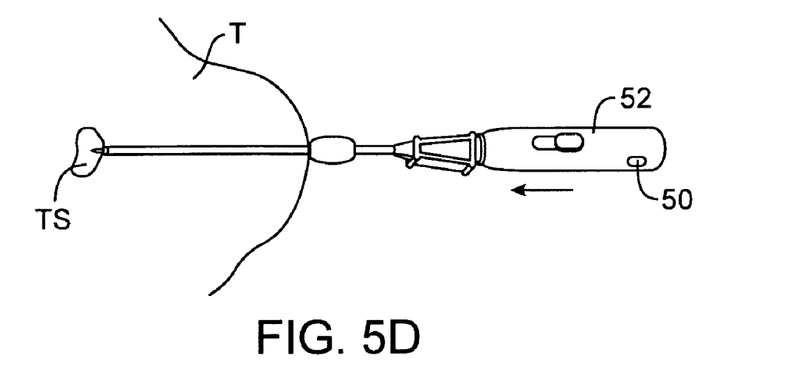
Figure 5E:
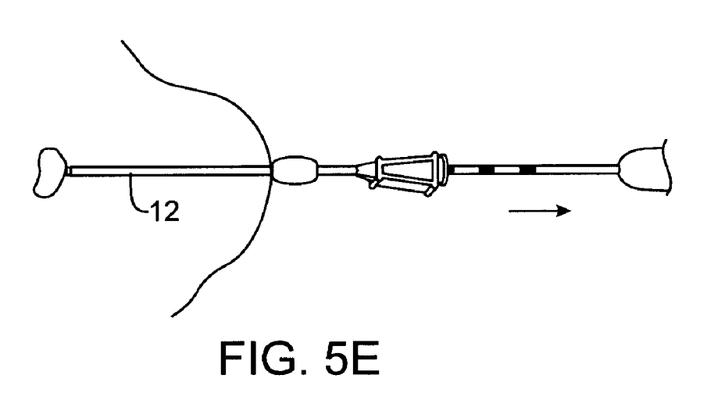
Figure 5F:
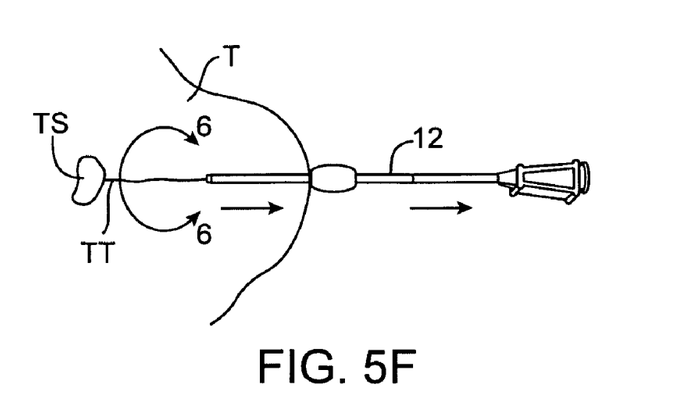
Figure 6:
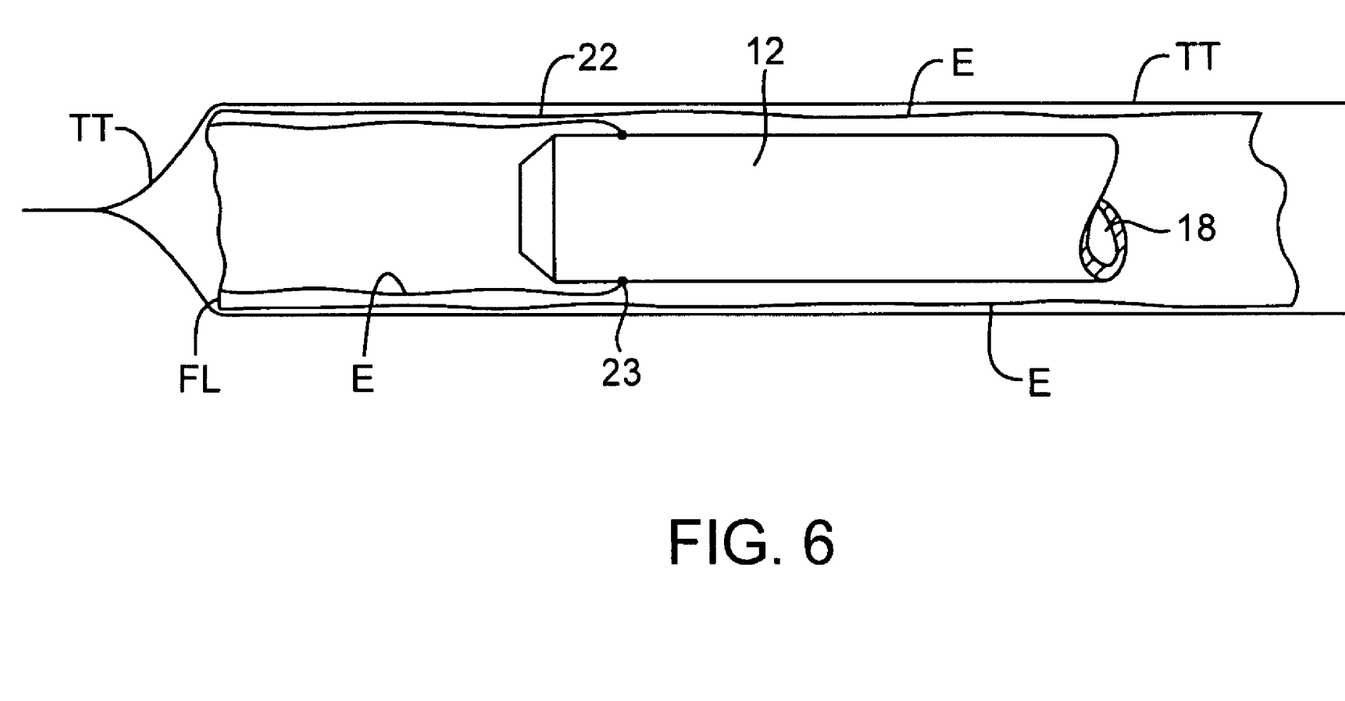
FIG. 6 is a detail view 6-6 of FIG. 5F illustrating invagination of the protective sleeve as the cannula is withdrawn from a tissue tract.

After the biopsy instrument 50 is used to obtain one or more samples from target site TS, as shown in FIG. 5D, the biopsy device 50 and sample may be withdrawn from the cannula 12 in the direction of the arrow shown in FIG. 5E. The cannula 12 may then be withdrawn by pulling on handle 52 (FIG. 5D) in the direction of the arrow shown in FIG. 5F. Withdrawal of the cannula 12 by pulling on handle 52 draws back on the end 23 of the protective sleeve attached to the cannula (FIG. 6). Such pulling of the protective sleeve 22 causes the attached end 23 to be drawn inwardly within itself, as shown in FIG. 6. Thus, a fold line FL in the sleeve 22 is created, with the fold line moving outwardly through the tissue tract TT (FIG. 5F) at a rate approximately one-half of that at which the cannula is withdrawn. It will be appreciated that the exterior E of the sheath is thus withdrawn into the initial lumen of the sheath and enveloped within the sheath, thus reducing any chance that tumor cells will be inadvertently pulled back to seed through the tissue tract as the cannula 12 is withdrawn. Equally important, the portion of the exterior surface E of sleeve 22 which remains in contact with tissue will be substantially stationary, i.e., it will not be moving axially relative to the tissue tract. Thus, the combination of exterior immobility with a version of the exterior into the sleeve itself assures that any risk of cell seeding will be significantly reduced.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for obtaining a sample from solid tissue, said method comprising:
   accessing a site in the solid tissue by advancing a cannula covered with a protective sleeve through the solid tissue, wherein advancement of the cannula creates a tissue tract;
   obtaining the sample through a central passage of the cannula, wherein obtaining the sample comprises advancing a stylet from the cannula to capture sample in a recess on the stylet and advancing the cannula to excise the captured sample; and
   withdrawing the cannula, wherein a distal region of the cannula is fixedly attached to a distal portion of the sleeve so that the distal portion of the sleeve is pulled by the cannula to inwardly evert as the cannula is withdrawn, through the tissue tract.

2. A method as in claim 1, wherein a sliding friction between the sleeve and the cannula is less than a sliding friction between the sleeve and the tissue so that axial sliding of the sleeve in the tissue is inhibited.

3. A method as in claim 1, wherein accessing comprises advancing the cannula with the stylet positioned in the central passage, wherein the stylet has a sharpened tip which extends distally beyond a distal end of the cannula.

4. A method as in claim 1, wherein accessing comprises:
   positioning the protective sleeve in a furled configuration at a percutaneous access site on a tissue surface; and
   advancing the cannula through the access site to unfurl the sleeve and cover the cannula as the cannula is advanced.

5. A method as in claim 4, wherein advancing the cannula through the access site comprises capturing a free end of the protective sleeve, wherein the captured end is pulled by the cannula.

6. A method for obtaining a sample from solid tissue, said method comprising:
   accessing a site in the solid tissue by advancing a cannula covered with a protective sleeve through the solid tissue, wherein the cannula has a central passage with a stylet positioned therein with a sharpened tip which extends distally beyond a distal end of the cannula to create a tissue tract while the cannula is advanced;
   obtaining the sample through a central passage of the cannula by advancing the stylet from the cannula to capture sample in a recess on the stylet and advancing the cannula to excuse the captured sample; and
   withdrawing the cannula through the protective sleeve, wherein a sliding friction between the sleeve and the cannula is less than a sliding friction between the sleeve and the tissue tract so that axial sliding of the sleeve in the tissue is inhibited.

7. A method as in claim 6, wherein a distal region of the cannula is fixedly attached to a distal portion of the sleeve so that the distal portion of the sleeve is pulled by the cannula to inwardly evert as the catheter is withdrawn.

8. A method as in claim 6, wherein accessing comprises positioning the protective sleeve in a furled configuration at a percutaneous access site on a tissue surface; and
   advancing the cannula through the access site to unfurl the sleeve and cover the cannula as the cannula is advanced.

9. A method as in claim 8, advancing the cannula through the access site comprises capturing a free end of the protective sleeve, wherein the captured end is pulled by the cannula.

* * * * *